(12) United States Patent
Funda et al.

(10) Patent No.: US 9,248,106 B2
(45) Date of Patent: Feb. 2, 2016

(54) BEADLETS COMPRISING HOP ACID SALTS IN A PROTEIN MATRIX

(71) Applicant: DSM IP ASSETS B.V., Heerlen (NL)

(72) Inventors: Elger Funda, Basel (CH); Dominique Joas, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/372,302

(22) PCT Filed: Dec. 28, 2012

(86) PCT No.: PCT/EP2012/077023
§ 371 (c)(1),
(2) Date: Jul. 15, 2014

(87) PCT Pub. No.: WO2013/107607
PCT Pub. Date: Jul. 25, 2013

(65) Prior Publication Data
US 2014/0370106 A1    Dec. 18, 2014

(30) Foreign Application Priority Data
Jan. 19, 2012    (EP) .................................... 12151681

(51) Int. Cl.
| | |
|---|---|
| *A61K 31/12* | (2006.01) |
| *A61K 9/16* | (2006.01) |
| *C12C 3/00* | (2006.01) |
| *C12H 1/04* | (2006.01) |
| *A23L 1/10* | (2006.01) |
| *A61K 31/122* | (2006.01) |
| *A23K 1/00* | (2006.01) |
| *A23K 1/16* | (2006.01) |
| *A23K 1/17* | (2006.01) |

(52) U.S. Cl.
CPC ............... *A61K 31/122* (2013.01); *A23K 1/002* (2013.01); *A23K 1/004* (2013.01); *A23K 1/1609* (2013.01); *A23K 1/1631* (2013.01); *A23K 1/17* (2013.01); *A61K 9/1658* (2013.01)

(58) Field of Classification Search
None
See application file for complete search history.

(56) References Cited

U.S. PATENT DOCUMENTS

| | | |
|---|---|---|
| 6,444,227 B1 | 9/2002 | Leuenberger et al. |
| 2006/0013870 A1 | 1/2006 | Kuhrts |
| 2009/0092735 A1 | 4/2009 | Yamaguchi et al. |
| 2012/0115960 A1* | 5/2012 | Garden et al. ................ 514/689 |

FOREIGN PATENT DOCUMENTS

| | | |
|---|---|---|
| CN | 1735350 | 2/2006 |
| WO | WO 2004/062382 | 7/2004 |

OTHER PUBLICATIONS

U.S. Patent Documents—None.*
Non-Patent Documents—None.*
International Search Report for PCT/EP2012/077023 mailed May 27, 2013.
Chinese Official Action for Application No. 2012-80067665.3 mailed Jun. 30, 2015.

* cited by examiner

*Primary Examiner* — Jeffrey T Palenik
(74) *Attorney, Agent, or Firm* — Nixon & Vanderhye P.C.

(57) ABSTRACT

The present invention relates a process of production of beadlets comprising at least one hop acid salt in a matrix comprising at least one protein, to such beadlets and to the use of such specific beadlets in feed as well as in feed premixes.

9 Claims, No Drawings

BEADLETS COMPRISING HOP ACID SALTS IN A PROTEIN MATRIX

This application is the U.S. national phase of International Application No. PCT/EP2012/077023 filed 28 Dec. 2012 which designated the U.S. and claims priority to EP 12151681.9 filed 19 Jan. 2012, the entire contents of each of which are hereby incorporated by reference.

The present invention relates to a process for production of beadlets comprising hop acids salts in a matrix comprising at least one protein, to such beadlets and to the use of such specific beadlets.

Hop acids are used in farm animals to improve overall animal performance since they act in the digestive system of the animal as mild antibiotics or ionophores (WO2010/123571). Hop acids include but are not limited to alpha acids, beta acids and their isomerized forms. Beta acids include lupulone, colupulone, adlupulone as well as other analogs. Alpha acids include humulone, cohumulone, adhumulone, posthumulone, prehumulone, as well as other analogs.

The knowledge of the antimicrobial properties of the hop acids dates back a very long time, and the benefit of natural antimicrobial to the growth and health performance of farm animals in industrial production is also undisputed and their safety to consumption is also very well documented in the art. However, the use of hop acids in animal feeding is practically not possible in the industry because of the instability of the compounds when exposed to air and humidity in the feed.

Therefore, there is a need in the industry to provide stabilized forms of hop acids and hop extracts which are resistant to moisture and oxygen during storage, when used in a feed or a feed premix, moreover, hop acids should also be stable when subjecting the feed containing hop acids to the harsh conditions of feed pelleting at high temperature which is a standard in the swine and broiler feed industry.

A very typical form of formulation of substances used in consumer products (such as for example food products) are powders. Powders can be produced by spray drying or spray granulation processes but they do not allow stabilisation of hop acids such that they are not degraded in the feed or feed premix.

Another well known form of preparations are beadlets. Beadlets provide superior handling properties in that they are not dusty and possess good flowability characteristics. Beadlets are solely known for fat-soluble substances.

Beadlets (comprising fat-soluble substances) and their methods of productions are known from the prior art. These beadlets comprise fat-soluble (lipophilic, hydrophobic) substances. Such beadlets and their process for production are for example known from US2006/0115534 and U.S. Pat. No. 4,670,247. These beadlets usually have good storage stability, but the production of such beadlets requires an emulsification or dispersion step to distribute the water-insoluble active in the aqueous matrix phase. Therefore, the matrix material needs to have emulsifying properties or an additional emulsifier is required.

The goal of the present invention was to find a process for producing formulations comprising hop acids, which allows producing storage stable and pelleting stable formulations using a simple process and that can be produced at a cost compatible with the feed and feed additive industry.

Surprisingly, it has been found that using hop acids in their deprotonated form at high pH allows their formulation in the powder catch process without the need for an emulsification step. The formulations are in the form of beadlets having the above mentioned advantages. The beadlets comprise one or more hop acids salts and one protein or protein mixture as a matrix material and are devoid of antioxidant. Furthermore these beadlets are coated with a layer of the powder catch medium.

Therefore, the present invention relates to a process for preparing beadlets, which comprise at least one hop acid salt, comprising:
(a) forming an aqueous solution of
  (i) at least one hop acid salt and
  (ii) at least one protein or protein mixture,
(b) adjusting the pH of the solution to pH greater than 9
(c) converting the solution into a dry powder by spray drying into a collecting powder.

The aqueous solution is preferably adjusted to a pH greater than 9, more preferably greater than 9.5 in order to prevent the precipitation of hop acid salts.

Such a process is known from the prior art. It can be found for example in U.S. Pat. No. 6,444,227 or WO04062382.

Preferred hop acids according to the present invention include but are not limited to alpha acids, beta acids and their isomerized forms. Beta acids include lupulone, colupulone, adlupulone as well as other analogs and mixtures thereof. Alpha acids include humulone, cohumulone, adhumulone, posthumulone, prehumulone, as well as other analogs and mixtures thereof. Hop acid salts include metal salts like sodium or potassium or alkaline earth metal salts like calcium and magnesium. Preferred salts for all embodiments of the present invention are potassium salts, and preferred hop acids are beta acids.

Therefore a preferred embodiment of the present invention relates to a process for preparing beadlets, which comprise at least one hop beta acid salt. More preferred hop acid salt is a mixture of hop beta acid salts primarily comprising lupulone, colupulone, and adlupulone salts. More preferred salt is potassium salt.

The hop acids are formulated in a beadlet by a matrix material, which comprises at least one protein or protein mixture.

Proteins are large organic compounds made of amino acids arranged in a linear chain and joined together by peptide bonds between the carboxyl and amino groups of adjacent amino acid residues. All living tissues (animals, human and plants) contain proteins.

Proteins are available as isolates, concentrates, meals and hydrolysates. Protein isolates contain more than 90% protein. Protein concentrates contain 60-90% protein. Protein meals contain less than 60% protein. In protein hydrolysates, a part of the peptide bonds is broken either chemically, e.g. by acid or enzymatically. Thereby the molecular weight and the degree of polymerisation of the protein is reduced. The amount of hydrolysis is described by the degree of hydrolysis (DH). The DH is the percentage of broken peptide bonds compared to all peptide bonds. Therefore a DH of 0% describes a native protein while a DH of 100% describes a completely hydrolysed protein.

The protein content in plants is very small. In contrast to plants, animal and human bodies are composed largely of proteins.

Preferred sources of plant proteins are for example peas, beans (such as soya beans, castor beans, etc), lupins, cotton, potatoes, sweet potatoes, manioc, rapeseed, sunflowers, sesame, linseed, safflower, lentils, nuts, wheat, rice, maize, barley, rye, oats and sorghum.

Preferred sources of animal proteins are for example blood, bones, skin and milk and eggs.

Preferred sources of microbial proteins are for example bacteria or yeasts.

For the invention of the present patent application the following proteins are more preferred: gelatines (especially fish and poultry), hydrolysed gelatines and milk proteins (casein, whey proteins). Besides native protein isolates, concentrates or meals, proteins can be modified either mechanically, thermally, chemically or enzymatically. Partial denaturation of the protein e.g. by heat treat may be used to improve the gel-forming properties of the protein. The protein may also be crosslinked e.g. enzymatically by transglutaminase. To improve solubility or viscosity, the protein may be partially hydrolysed either chemically or enzymatically by proteases.

In the context, the term "proteins" includes native proteins as isolates, concentrates or meals as well as modified, denatured or crosslinked proteins or hydrolysates.

Therefore the present invention also related to a process as described above, wherein the protein is a protein isolate, concentrate or meal.

The present invention also relates to a process as described above, wherein the protein is a protein hydrolysate.

The present invention also relates to a process as described above, wherein the protein is a heat-treated.

The present invention also relates to a process as described above, wherein the protein is crosslinked.

The matrix of the beadlets of the present invention can also comprise additional compounds, such as sugars or sugar alcohols. Sugar refers to any monosaccharide or disaccharide (preferred is sorbitol).

The matrix of the beadlets may also comprise further excipients, such as plasticizers or antioxidants.

A preferred process according to the present invention is a powder catch process. Such a process is known from the prior art (for example from WO04062382). As a result of such a powder catch process the beadlets are covered by a layer of the powder.

Therefore, the beadlets produced according to this process are preferably covered by a layer of the powder catch medium. This layer (coating) is in the form of a powder coating.

The powder catch medium is a compound (or a mixture of compounds), which is able to absorb moisture and to form a powder coating. Suitable powder catch media are i.e. starches, silicate or phosphate compounds. Preferred powder catch media are starches (such as i.e. corn starch), calcium silicate, calcium aluminium silicate and tri-calcium phosphate. Most preferred are starches, especially corn starch.

Beadlets are a well known form of formulation for fat-soluble substances. An important advantage of the generally spherical beadlets is that they are not dusty and that they show excellent free flowing characteristics, which are very desirable for manufacturing and formulating operations.

Usually the size of a beadlet is from 50 μm to 1,000 μm (preferably from 250 μm to 850 μm). The sizes can be smaller or larger. The size of a beadlet can be determined according to well known methods, such as (scanning) electron microscopy.

A suitable method to produce beadlets as disclosed and described above is for example described in WO 2004/062382.

The process according to the present invention surprisingly allows producing beadlets with a high stabilization of the hop acids salts in the product itself and when mixed with a feed or feed premix and without requiring an emulsification step.

The process as described in the present patent application can be used to produce beadlets with an amount of hop acid salts adjusted to the needs of the feed industry. The amount can be as low as 5 wt-%, based on the total weight of the beadlets, Usually the content of hop acid salts in the beadlets is comprised between 5 wt-% and 25 wt. %, preferably between 10 wt-% and 15 wt. %, based on the total weight of the beadlets.

A preferred process according to the present invention relates to a process as described above wherein the beadlets comprise 5 to 25 wt-%, based on the total weight of the beadlets, of at least one hop acid salt, preferably, 10 to 15 wt.-% based on the total weight of the beadlets.

A preferred process according to present invention relates to a process wherein the beadlets comprise at least 30 wt-%, based on the total weight of the beadlets, more preferred at least 50 wt-%, of at least one protein or protein mixture (matrix material) and of the powder coating layer.

A preferred process according to present invention relates to a process wherein the beadlets comprise at least 3 wt-%, based on the total weight of the beadlets, of powder coating layer.

A more preferred process according to present invention relates to a process wherein the beadlets comprise
(i) 5 wt-% to 25 wt-%, preferably 10 wt-% to 20 wt-%, more preferably 10 wt-% to 15 wt-%, based on the total weight of the beadlets, of at least one hop acid salt, and
(ii) 30 wt-% to 90 wt-%, preferably 50 wt-% to 85 wt-%, based on the total weight of the beadlets, of at least one protein or protein mixture, and
(iii) 3 wt-% to 50 wt-%, preferably 5 wt-% to 20 wt-%, based on the total weight of the beadlets, of powder coating.

The matrix of the beadlets of the present invention as described above can also comprise additional compounds. Such compounds can be any kind of auxiliaries used in the field of beadlet producing and/or food and feed technology. A preferred compound is sugar or sugar alcohol (sorbitol). A preferred antioxidant used in the beadlets of the present invention is EMQ.

Beadlets comprising a high amount (at least 25 wt-%) of hop acid salts in a matrix comprising at least one protein or protein mixture are not known from the prior art.

A further embodiment of the present invention relates to beadlets (B1) comprising
(i) 5 to 25 wt-%, based on the total weight of the beadlets, of at least one hop acid salt and
(ii) at least one protein or protein mixture.

The invention also relates to beadlets (B2) comprising
(i) 10 to 15 wt-%, based on the total weight of the beadlets, of at least one hop acid salt, and
(ii) at least one protein or protein mixture.

Preferred beadlets (B1') according to present invention comprise
(i) 5 to 25 wt-%, based on the total weight of the beadlets, of at least one hop acid salt and
(ii) at least 30 wt-%, based on the total weight of the beadlets, of at least one protein or protein mixture.

The beadlets (B2') according to present invention comprise
(i) 10 to 15 wt-%, based on the total weight of the beadlets, of at least one hop acid salt, and
(ii) at least 50 wt-%, based on the total weight of the beadlets, of at least one protein or protein mixture.

Preferred hop acid salts in the beadlets of the present invention are potassium salts of hop beta acids.

Preferred starch covered beadlets according to present invention comprise at least 3 wt-%, based on the total weight of the beadlets, of the powder coating layer. Therefore beadlets (B1), (B1'), (B2), and (B2') preferably comprise at least 5 wt-%, based on the total weight of the beadlets, of powder coating layer.

More preferred beadlets according to the present invention (B3) comprise
- (i) 5 wt-% to 25 wt-%, preferably 10 wt-% to 15 wt-%, based on the total weight of the beadlets, of at least one hop acid salt, and
- (ii) 30 wt-% to 90 wt-%, preferably 50 wt-% to 85 wt-%, based on the total weight of the beadlets, of at least one protein from a plant source (such as peas, soya, castor beans, cotton, lupins, potatoes, sweet potatoes, manioc, rapeseed, sunflowers, sesame, linseed, safflower, lentils, nuts, wheat, rice, maize, barley, rye, oats and sorghum), an animal source (such as blood, bones, skin, milk and eggs), or a microbial source (such as bacteria and yeasts), and
- (iii) 3 wt-% to 50 wt-%, preferably 5 wt-% to 20 wt-%, based on the total weight of the beadlets, of powder coating chosen from the group consisting of starches (preferably corn starch), silicate and phosphate compounds.

Further, more preferred beadlets are beadlets (B1), (B1'), (B2), (B2'), and (B3) additionally comprising a sugar alcohol (sorbitol). These beadlets (B4) comprise 5 to 25 wt-%, preferably 10 to 20 wt-%, based on the total weight of the beadlets, of sorbitol.

A further embodiment according to the present invention relates to the use of the beadlets (B1), (B1'), (B2), (B2'), (B3), and (B4) in feed products as well in the production of feed products.

Feed products in the context of the present invention comprise liquid and solid feed products as well as paste-like and or gel like. The feed products comprise feed for animals (especially ruminants, poultry and swine).

Suitable animal feed products can be in any commonly used form.

Therefore a further embodiment of the present invention relates to animal feed products and to animal feed additives comprising beadlets as described above.

Premixes are a convenient usage form for the feed producers but are a critical medium for various ingredients due to pH, ionic strength and water activity values, which can negatively affect stability of various ingredients. But the beadlets according to the present invention eliminate (or at least strongly minimize) such problems.

The beadlets according to the present invention can also be used in premixes for feed products.

A further embodiment of the present invention is a premix for feed products comprising beadlets according to the present invention.

Functional ingredients like vitamins and trace elements are often added to feed products as well as to premixes.

The following examples serve to illustrate the invention. The percentages are expressed in weight percentages and the temperatures are degrees Celsius, if not otherwise defined.

EXAMPLE 1

Formulation of Hop Beta Acid Potassium Salt in a Matrix of Whey Protein 20 g hop acids extract (44.9% beta acids potassium salts) and 30 g whey protein and 20 g sorbitol were dissolved in 100 g water with stirring. About 150 g of the solution was sprayed in a spraying pan in a bed of fluidized starch at about 25° C. by means of a rotating spraying nozzle. The so-obtained beadlets were separated from excess starch by sieving and dried with a fluid bed drier. There were obtained ca. 145 g of dry powder having a beta acids content of 5.5%.

EXAMPLE 2

Stability of Hop Acid Salts Beadlets in a Whey Protein Matrix

The product from examples 1 was stored for 1 week at 25° C. Stability was measured as recovery of beta acids content compared to initial. Stability after 1 week was 97%.

The invention claimed is:

1. Process for preparing beadlets, which comprise at least one hop acid salt, comprising:
   (a) forming an aqueous solution of
      (i) at least a hop acid salt and
      (ii) at least one protein or protein mixture,
   (b) adjusting the pH of the solution to pH greater than 9
   (c) converting the solution into a dry powder by spray drying into a collecting powder.

2. A process according to claim 1, wherein the hop acid salt is a mixture primarily comprising lupulone, colupulone, and adlupulone salts.

3. A process according to claim 1, wherein the hop acid salt is a potassium salt.

4. A process according to claim 1, wherein the proteins are chosen from a plant source such as peas, soya, castor beans, cotton, lupins, potatoes, sweet potatoes, manioc, rapeseed, sunflowers, sesame, linseed, safflower, lentils, nuts, wheat, rice, maize, barley, rye, oats and sorghum, an animal source such as blood, bones, skin, milk and eggs or a microbial source such as bacteria and yeasts.

5. A process according to claim 4 wherein the proteins are chosen from the group consisting of gelatines, hydrolysed gelatines and milk proteins such as whey protein or casein.

6. A process according to claim 1, wherein the beadlets are covered by a powder coating.

7. A process according to claim 1, wherein the beadlets comprise 10 wt.-% to 15 wt-%, based on the total weight of the beadlets, of at least one hop acid salt.

8. A process according to claim 1, wherein the beadlets comprise at least 30 wt-%, preferably at least 50 wt-%, based on the total weight of the beadlets, of at least one protein or protein mixture and of the powder coating layer.

9. A process according to claim 1, wherein the beadlets comprise at least 3 wt-%, based on the total weight of the beadlets, of powder coating layer.

* * * * *